(12) United States Patent
Duval et al.

(10) Patent No.: US 12,070,321 B2
(45) Date of Patent: *Aug. 27, 2024

(54) DEVICES, SYSTEMS, AND METHODS FOR DETERMINING INFLAMMATION AND/OR FIBROSIS

(71) Applicant: Boston Scientific Scimed, Inc., Maple Grove, MN (US)

(72) Inventors: George Wilfred Duval, Sudbury, MA (US); Namita M. Kallur, Hayward, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 590 days.

This patent is subject to a terminal disclaimer.

(21) Appl. No.: 17/348,954

(22) Filed: Jun. 16, 2021

(65) Prior Publication Data
US 2021/0307674 A1 Oct. 7, 2021

Related U.S. Application Data

(63) Continuation of application No. 16/458,224, filed on Jul. 1, 2019, now Pat. No. 11,058,345.
(Continued)

(51) Int. Cl.
*A61B 5/00* (2006.01)
*A61B 5/07* (2006.01)
(Continued)

(52) U.S. Cl.
CPC ............ *A61B 5/4216* (2013.01); *A61B 5/073* (2013.01); *A61B 5/1076* (2013.01);
(Continued)

(58) Field of Classification Search
CPC ......... A61B 5/4216; A61B 5/42; A61B 5/073; A61B 5/1076; A61B 5/4238;
(Continued)

(56) References Cited

U.S. PATENT DOCUMENTS

| | | |
|---|---|---|
| 5,666,467 A | 9/1997 | Colak |
| 2004/0230108 A1 | 11/2004 | Melker et al. |

(Continued)

FOREIGN PATENT DOCUMENTS

| | | |
|---|---|---|
| CN | 103845695 A | 6/2014 |
| RU | 2 556 573 C1 | 7/2015 |
| WO | 2013/059732 A1 | 4/2013 |
| WO | 2017/074505 A1 | 5/2017 |

OTHER PUBLICATIONS

Hubert Allgayer et al., "Transabdominal ultrasound in inflammatory bowel disease. Conventional and recently developed techniques—Update," Medical Ultrasonography, 2011, pp. 302-313, vol. 13, No. 4 (12 pages).

Fredrik Saevik et al., "Bowel Perfusion Measured with Dynamic Contrast-enhanced Ultrasound Predicts Treatment Outcome in Patients with Crohn's Disease," Inflammatory Bowel Diseases, Nov. 2014, pp. 2029-2037, vol. 20, No. 11 (9 pages).

(Continued)

*Primary Examiner* — Scott M. Getzow
(74) *Attorney, Agent, or Firm* — Bookoff McAndrews, PLLC (57) ABSTRACT

A method for evaluating a gastrointestinal tract of a subject may comprise using a sensor located in the subject to obtain data regarding qualities of a tissue of the gastrointestinal tract; using the obtained data, determining a measure of perfusion of blood in the tissue; using the obtained data, determining a measure of thickness of the tissue; using the measure of perfusion and the measure of thickness, determining a measure of inflammation of the tissue; and using one or more of the measure of perfusion, the measure of thickness, and the measure of inflammation, classifying a state of the tissue.

20 Claims, 4 Drawing Sheets

Related U.S. Application Data (60) Provisional application No. 62/694,163, filed on Jul. 5, 2018.

(51) Int. Cl.
*A61B 5/107* (2006.01)
*A61B 5/026* (2006.01)
*A61B 5/0295* (2006.01)

(52) U.S. Cl.
CPC .......... *A61B 5/4238* (2013.01); *A61B 5/4255* (2013.01); *A61B 5/7264* (2013.01); *A61B 5/0086* (2013.01); *A61B 5/0261* (2013.01); *A61B 5/0295* (2013.01); *A61B 5/1072* (2013.01); *A61B 5/4233* (2013.01); *A61B 5/6861* (2013.01)

(58) Field of Classification Search
CPC ................ A61B 5/4255; A61B 5/7264; A61B 5/0086; A61B 5/0261; A61B 5/0295; A61B 5/1072; A61B 5/4233; A61B 5/6861; G16H 50/30
See application file for complete search history.

(56) References Cited

U.S. PATENT DOCUMENTS

| | | |
|---|---|---|
| 2013/0323720 A1 | 12/2013 | Watelet et al. |
| 2015/0351714 A1 | 12/2015 | De Backer |
| 2016/0338634 A1 | 11/2016 | Neu et al. |
| 2018/0103852 A1 | 4/2018 | Dagdeviren et al. |
| 2018/0360327 A1* | 12/2018 | Duval .................... A61B 5/349 |

OTHER PUBLICATIONS

Ryan W. Stidham et al., "Imaging of intestinal fibrosis: current challenges and future methods," United European Gastroenterology Journal, 2016, pp. 515-522, vol. 4, No. 4 (8 pages).

Thomas Scholbach et al., "Dynamic Tissue Perfusion Measurement in the Intestinal Wall—Correlation with Ulcerative Colitis," Journal of Medical Ultrasound, 2010, pp. 62-70, vol. 18, No. 2 (9 pages).

Emilio Quaia et al., "Time-Intensity Curves Obtained after Microbubble Injection Can Be Used to Differentiate Responders from Nonresponders among Patients with Clinically Active Crohn Disease after 6 Weeks of Pharmacologic Treatment," Radiology, 2016, vol. 281, No. 2, pp. 606-616 (11 pages).

* cited by examiner

DEVICES, SYSTEMS, AND METHODS FOR DETERMINING INFLAMMATION AND/OR FIBROSIS

CROSS-REFERENCE TO RELATED APPLICATIONS

This application is a continuation under 37 CFR § 1.53(b) of U.S. application Ser. No. 16/458,224, filed on Jul. 1, 2019, which claims the benefit of priority from U.S. Provisional Application No. 62/694,163, filed on Jul. 5, 2018, which are incorporated by reference herein in their entireties.

TECHNICAL FIELD

The present disclosure relates generally to devices, systems, and/or methods for diagnosing and/or monitoring disease by, for example, determining inflammation and/or fibrosis. More specifically, aspects of the present disclosure pertain to devices, systems, and/or methods for scoring inflammation and determining fibrosis using indices for perfusion and tissue thickening.

BACKGROUND

Inflammatory Bowel Disease ("IBD") is a chronic disorder characterized by chronic inflammation in the gastrointestinal ("GI") tract. The disease affects 5-6 million people worldwide, with approximately 1.6 million sufferers in the United States. Patients and health care providers may spend substantial amounts of money per year treating IBD, with annual direct costs estimated between $11-28 billion in the United States. Moreover, people with IBD may have longer and more expensive hospitalizations with higher readmission rates than people without IBD.

There are two main types of IBD: Ulcerative Colitis ("UC") and Crohn's Disease ("CD"). CD can affect any part of the digestive system and is characterized with transmural involvement. Symptoms of CD include abdominal pain, fever, cramping, rectal bleeding, and frequent diarrhea. The peak age for CD disease onset is between 15-35 years. UC affects the colon only, with mucosal involvement. UC carries mild to severe symptoms, which are similar to the symptoms of CD. With UC, complications may be less frequent than with CD. Colectomy may be used to treat UC. The peak age of disease onset for UC is between 15-30 and 50-70 years old. 55% of IBD patients have UC, and 45% of IBD patients have CD.

A patient's IBD can grow more severe over time. For example, in early stages of disease, IBD may affect the mucosal lining of the small bowel and/or colon. As time passes, IBD may progress and affect the entire bowel and/or colon wall. On the other hand, treatment of IBD may result in alleviation of symptoms. Conventional treatments focus on addressing present symptoms. However, conventional treatments lack an ability to robustly evaluate inflammation of the GI tract and the presence of fibrosis. Techniques such as MRI have limited resolution and do not provide real-time information. Color enhanced ultrasound devices are not standardized, are often unavailable, and add substantial costs. For example, color enhanced ultrasound may not be able to be performed in an endoscopy suite. Without information about fibrotic attributes of a GI tract, a physician's ability to effectively treat disease may be limited.

SUMMARY

Examples of the present disclosure relate to, among other things, devices, systems, and/or methods for diagnosing and/or monitoring disease by, for example, determining inflammation and/or fibrosis. Each of the examples disclosed herein may include one or more of the features described in connection with any of the other disclosed examples.

A method for evaluating a gastrointestinal tract of a may comprise using data regarding qualities of a tissue of the gastrointestinal tract, determining a measure of perfusion of blood in the tissue; using the data, determining a measure of thickness of the tissue; using the measure of perfusion and the measure of thickness, determining a measure of inflammation of the tissue; and using one or more of the measure of perfusion, the measure of thickness, and the measure of inflammation, classifying a state of the tissue.

Any method described herein may include one or more of the features or steps described below. Classifying a state of the tissue may include classifying a fibrotic attribute of the tissue. Classifying a fibrotic attribute may include determining whether the tissue is fibrotic. The measure of perfusion may be a perfusion index. The perfusion index may be a ratio of an amount of pulsatile light to an amount of total light. Determining a measure of inflammation may comprise: applying a first function to the measure of perfusion; and applying a second function to the measure of thickness. Determining a measure of inflammation may further comprise adding the result of the first function and the result of the second function. Applying the first function may include applying a weighting value. Applying the first function may include applying a sigmoid function. Applying the second function may include applying a sigmoid function. Applying the first function may include calculating a difference between the measure of perfusion and a reference measure of perfusion. Using one or more of the measure of perfusion, the measure of thickness, and the measure of inflammation may include using at least two of the measure of perfusion, the measure of thickness, and the measure of inflammation. Using one or more of the measure of perfusion, the measure of thickness, and the measure of inflammation may include using each of the measure of perfusion, the measure of thickness, and the measure of inflammation. Using the measure of perfusion, the measure of thickness, and the measure of inflammation may comprise categorizing the measure of perfusion and categorizing the measure of inflammation. The method may further comprise comparing the measure of inflammation to a reference measure of inflammation. The reference measure may be indicative of an amount of inflammation in a healthy tissue.

A method for evaluating a gastrointestinal tract of a subject may comprise using a sensor located in the subject to obtain data regarding qualities of a tissue of the gastrointestinal tract; using the obtained data, determining a measure of perfusion of blood in the tissue; using the obtained data, determining a measure of thickness of the tissue; using the measure of perfusion and the measure of thickness, determining a measure of inflammation of the tissue; and using one or more of the measure of perfusion, the measure of thickness, and the measure of inflammation, classifying a state of the tissue.

Any method described herein may include one or more of the features or steps described below. Classifying a state of the tissue may include classifying a fibrotic attribute of the tissue. The sensor may be an optical sensor located in a lumen of the gastrointestinal tract. The measure of perfusion may be a perfusion index. The perfusion index may be a ratio of an amount of pulsatile light received by the sensor to an amount of total light received by the sensor. Determining a measure of inflammation may comprise applying a first function to the measure of perfusion; and applying a second function to the measure of thickness. Determining a measure of inflammation may comprise adding the result of the first function and the result of the second function. Applying the first function may include applying a weighting value. Applying the first function may include applying a sigmoid function. Applying the first function may include calculating a difference between the measure of perfusion and a reference measure of perfusion. Using one or more of the measure of perfusion, the measure of thickness, and the measure of inflammation may include using each of the measure of perfusion, the measure of thickness, and the measure of inflammation. Using the measure of perfusion, the measure of thickness, and the measure of inflammation may comprise categorizing the measure of perfusion and categorizing the measure of inflammation. The method may further comprise comparing the measure of inflammation to a reference measure of inflammation.

In another example, a method for evaluating a gastrointestinal tract may comprise using a sensor located in a lumen of the gastrointestinal tract to obtain data regarding qualities of a tissue of the gastrointestinal tract; using the obtained data, determining a measure of perfusion of blood in the tissue; using the obtained data, determining a measure of thickness of the tissue; using the measure of perfusion and the measure of thickness, determining a measure of inflammation; and using the measure of inflammation, characterizing a fibrotic attribute of the tissue.

Any method described herein may include one or more of the features or steps described below. The sensor may be an optical sensor. The measure of perfusion may be a perfusion index. The perfusion index may be a ratio of an amount of pulsatile light received by the sensor to an amount of total light received by the sensor. Determining a measure of inflammation may comprise applying a first function to the measure of perfusion; and applying a second function to the measure of thickness. Determining a measure of inflammation may further comprise adding the result of the first function and the result of the second function. Applying the first function may include applying a weighting value. Applying the first function may include applying a sigmoid function.

In yet another example, a system for evaluating a gastrointestinal tract may comprise: a sensor configured to be placed in a gastrointestinal lumen of a patient to obtain data regarding tissue of the gastrointestinal tract; and a processor configured to: using the obtained data, determine a measure of perfusion of blood in the tissue; using the obtained data, determine a measure of thickness of the tissue; using the measure of perfusion and the measure of thickness, determine a measure of inflammation of the tissue; and using one or more of the measure of perfusion, the measure of thickness, and the measure of inflammation, classify a state of the tissue.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

The present disclosure is drawn to devices, systems, and/or methods for diagnosing and/or monitoring disease by, for example, determining inflammation and/or fibrosis. In particular, in at least some aspects, the devices, systems, and/or methods may be used to score inflammation and determine fibrosis using indices for perfusion and tissue thickening. The devices, systems, and methods for diagnosing and/or monitoring disease by, for example, scoring inflammation and determining fibrosis, described herein may also be used to monitor other medical conditions including, for example, other GI conditions such as irritable bowel syndrome, gastritis, gastroesophageal reflux disease (GERD), Barrett's esophagus, polyps, colorectal cancer, peptic ulcer, dysphagia, cholecystitis, diverticular disease, and celiac disease, and other medical conditions such as chronic asthma, chronic bronchitis, emphysema, gastritis, esophagitis, duodenal ulcer, and gastroenteritis. Although IBD monitoring or evaluation is referenced herein, reference to IBD should not be construed as limiting the possible applications of the disclosed systems. Although the disclosure is directed to identifying/diagnosing fibrosis and/or inflammation, aspects of the disclosure may also be used to diagnosing any of the above conditions or effects resulting from the above conditions.

Figure 1:
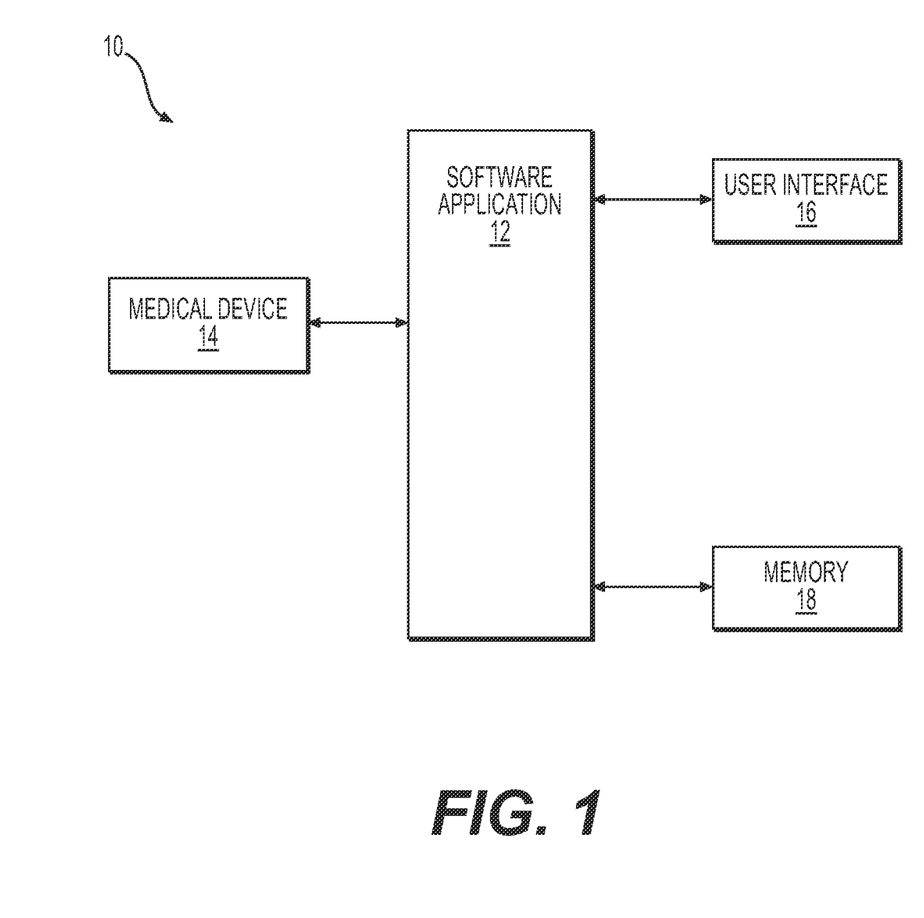
FIG. 1 depicts an exemplary system for scoring inflammation and determining fibrosis.

FIG. 1 depicts an exemplary system 10 for scoring inflammation and determining fibrosis. System 10 may include one or more software applications 12. Software application 12 may interface with, for example, a medical device 14, a user interface 16, and memory 18. Software application 12 may also interact with other software applications and/or other components, including sensors, medical records, therapy delivery systems, environmental data/sensors, medical personnel inputs, and/or user inputs.

Medical device 14 may include an imager capable of taking images including optical, infrared, thermal, or other images. Medical device 14 may also include other kinds of sensors, or inputs, including optical sensors, ultrasound sensors, and/or photodiodes. Medical device 14 may be capable of taking still images, video images, or both still and video images. Medical device 14 may be configured to transmit images or other data to a receiving device, either through a wired or a wireless connection. Medical device 14 may be, for example, a component of an endoscope system, a component of a tool deployed in a working port of an endoscope, a wireless endoscopic capsule, or one or more implantable monitors or other devices. In the case of an implantable monitor, such an implantable monitor may be permanently or temporarily implanted. Examples of medical devices suitable for use in connection with the present disclosure are described in U.S. patent application Ser. No. 16/011,925, filed Jun. 19, 2018, the complete disclosure of which is incorporated by reference herein.

Medical device 14 may be configured to capture data at one or more locations of the GI tract, including the esophagus, stomach, duodenum, small intestine, and/or colon. For example, during an endoscopy procedure, medical device 14 carried on an endoscope or a tool deployed in an endoscope (or simply the endoscope itself if equipped with suitable imaging components) may be advanced through various portions of the GI tract, and images or other data may be captured at numerous locations in a given portion or across portions. Medical device 14, a device carrying medical device 14, or another component of system 10, such as software application 12, may be capable of determining the location of the GI tract where data are captured. For example, medical device 14, a device carrying medical device 14, or another component of system 10, such as software application 12, may be able to determine whether images or other data were captured in the esophagus, the stomach, the ileum, the right colon, the transverse colon, the left colon, the rectum, or the jejunum, and, in certain embodiments, the precise location of such an organ. A medical device 14 carried by a wireless endoscopic capsule may capture data at various points as it traverses the GI tract. A medical device 14 which is part of an implantable monitor may be fixed in one location or may be capable of capturing data at multiple locations. For example, an implantable monitor may include numerous medical devices 14 at different locations within the GI tract. Medical device 14 may capture data continually or periodically.

Medical device 14 may be configured to capture data regarding perfusion of blood into a tissue of a GI tract. For example, medical device 14 may be configured to capture data relevant to blood's permeation into a tissue. To capture perfusion data, medical device 14 may include a light source and a receiver. Medical device 14 may include, for example, an optical sensor. For example, medical device 14 may include an LED light source and a photodiode receiver. In alternatives, medical device 14 may include alternative light sources such as light guides, fiber optics, or other light sources such as lasers pulsed at a specific wavelength (such as 530 nm and/or 930 nm) for trans-abdominal, non-invasive opto-acoustic excitation. Medical device 14 may also include alternative receivers such as acoustic transducer receivers. Medical device 14 may capture information regarding absorption and reflection of light waves in an area of interest in the GI tract. Information captured may include, for example, data indicative of the amount of pulsatile light (for example, varying light) received by a sensor of medical device 14. A sensor of medical device 14 may capture information about an AC component of light data captured, which may be indicative of an amount of pulsatile light measured. Information captured may also include, for example, data indicative of the amount of total light received. For example, a sensor of medical device 14 may capture information about a DC component of light data captured, which may be indicative of a total amount of light measured.

Medical device 14 may also capture data relevant to tissue thickness. Tissue thickening may be the result of increased blood flow to a tissue and possible obliteration of blood vessels and/or inflammation. Medical device 14 may include components configured to capture information relevant to thickness of an intestinal wall. For example, components of medical device 14 may include light sources at spaced intervals and thus may have a spatial diversity of light sources. Receivers may measure an amount of light reflected from a tissue. Different absorption rates in the tissue from the point of excitation for each spatially diverse transmitter may have a linear relationship to tissue thickness. Different depths of tissue may provide a different slope of the linear relationship, given a set of fixed distances between the light sources and a receiver.

An implantable device, including one or more medical devices 14, may be delivered via a natural orifice transluminal endoscopic surgery (NOTES) procedure, potentially during a colonoscopy. For example, during a colonoscopy, an incision may be made and a sensor may be implanted outside of the lumen on the omentum. Use of such a procedure may provide benefits including use of an endoscopy suite rather than an operating room. If medical devices 14 require a battery, a battery may be changed during a routine colonoscopy. Medical devices 14 may also be delivered via laproscopic surgery or a different surgical or non-surgical procedure.

Medical device 14 may be in communication either directly or indirectly with a software application 12, which may be stored on a processor or other suitable hardware. Medical device 14 may be connected with software application 12 by a wired or wireless connection. In the alternative, medical device 14 may be in communication with another type of processing unit. Software application 12 may run on a specialized device, a general-use smart phone or other portable device, and/or a personal computer. Software application 12 may also be part of an endoscope system, endoscope tool, wireless endoscopic capsule, or implantable device which also includes medical device 14. Software application 12 may be connected by a wired or wireless connection to a user interface 16 and/or memory 18.

Software application 12 or any other kind of processing unit may analyze signals received from medical device 14 and other inputs and may extract information from the data obtained by medical device 14 and the other inputs. Software application 12 or any other suitable component of system 10 may apply an algorithm to the signals or data from medical device 14 and other inputs.

Software application 12 may store information regarding algorithms, imaging data, or other data in memory 18. The data from inputs such as medical device 14 may be stored by software application 12 in memory 18 locally on a specialized device or a general-use device such as a smart phone or computer. Memory 18 may be used for short-term storage of information. For example, memory 18 may be RAM memory. Memory 18 may additionally or alternatively be used for longer-term storage of information. For example, memory 18 may be flash memory or solid state memory. In the alternative, the data from medical device 14 may be stored remotely in memory 18 by software application 12, for example in a cloud-based computing system.

User interface 16 may allow a user such as a medical professional, patient, or other user to access information stored in memory 18 or other information generated by software application 12. User interface 16 may allow a user to view and input data via a terminal, a hand-held device, a mobile device, a desktop device, or any other suitable device. User interface 16 may facilitate interactions by multiple users simultaneously or sequentially. User interface 16 may provide textual, graphical, video, audio, or other outputs.

Software application 12 may be configured to analyze data captured by medical device 14 related to, for example, tissue perfusion and/or tissue thickness, as described above. For example, software application 12 may be configured to apply algorithms to data captured by medical device 14. Algorithms may be stored in memory 18. Software application 12 may store the results or any component of its analyses in memory 18. Results or information stored in memory 18 may later be utilized for, example, tracking disease progression over time. Software application 12 may perform numerous analyses and generate various plots or other data.

Figure 2:
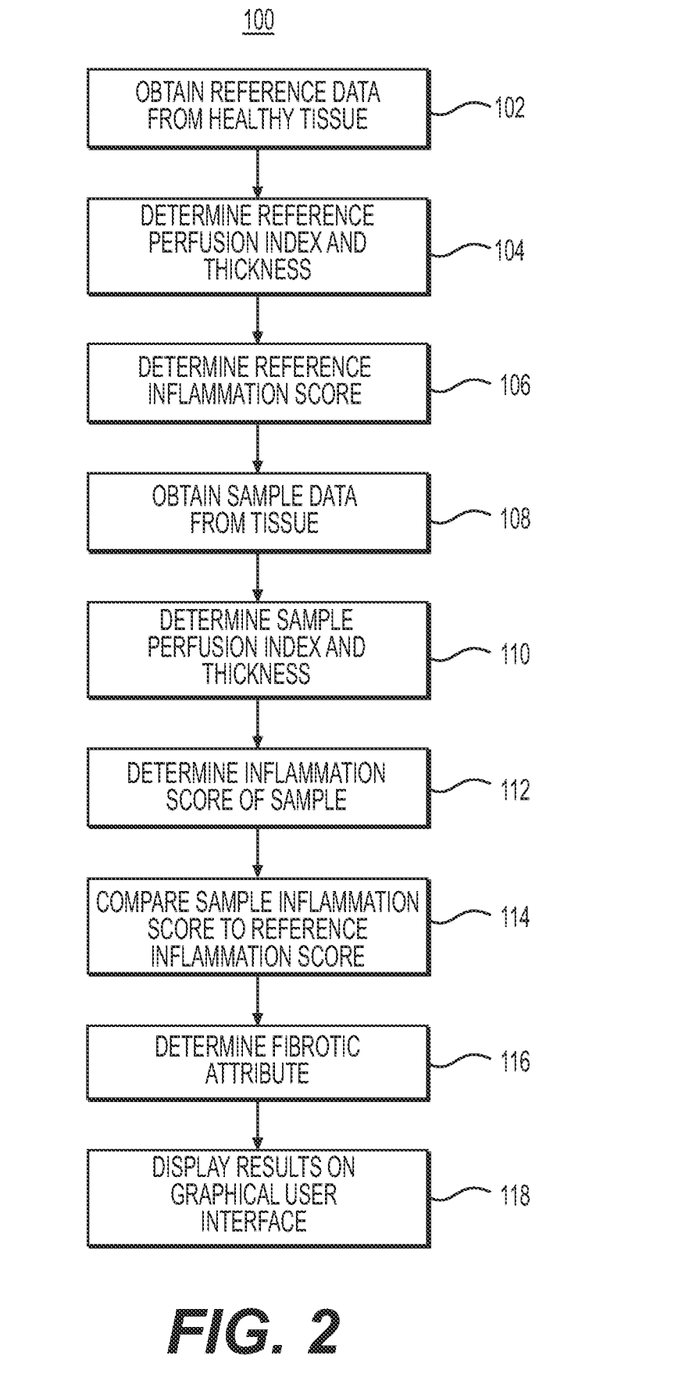
FIGS. 2-3 depict exemplary methods for scoring inflammation and determining fibrosis.

FIG. 2 shows a method 100 for evaluating characteristics of a GI tract. More specifically, FIG. 2 shows a method 100 for measuring, evaluating, and displaying fibrotic attributes of a GI tract. One or more steps of method 100 may be omitted and/or additional steps may be added to method 100. Any method resulting from omitted and/or additional steps is within the scope of the present disclosure. In step 102, a system such as system 10, described above with regard to FIG. 1, may obtain reference data from healthy tissue of a GI tract. For example, medical device 14 of system 10 may be used to obtain such data which may be, for example, indicative of an amount of light absorbed and/or reflected by a healthy tissue and may be gathered from, for example, a photo diode and/or optical array. Data obtained in step 102 may be from a subject for whom it is desired to characterize fibrotic attributes of a GI tract. In the alternative, data obtained in step 102 may be from a different subject, such as a healthy subject. In a further alternative, data obtained in step 102 may be data compiled from multiple subjects. For example, data obtained in step 102 may be obtained from a library of patient data.

In step 104, a component of system 10, such as software application 12, may characterize perfusion and/or tissue thickness of a healthy tissue based on the data obtained in step 102. To characterize perfusion, software application 12 may determine a perfusion index for a tissue sample. A perfusion index may be a measure of perfusion of blood into a tissue of the GI tract. A perfusion index may be determined using data collected by medical device 14. For example, data may be collected by a receiver, such as an optical receiver and/or a photodiode, of medical device 14. A perfusion index may include a ratio of an amount of pulsatile light (which may be an AC component) measured by medical device 14 to an amount of total light (which may be a DC component) measured by medical device 14. For example, a perfusion index may be calculated according to the following equation:

$$\text{Perfusion Index (\%)} = P = \frac{\text{Pulsatile (AC Component)}}{\text{Total Light (DC Component)}} \times 100\%$$

A perfusion index of less than 2% may be indicative of hypoperfusion. A perfusion index of between 2% and 4% may be indicative of moderate perfusion. A perfusion index between 4% and 8% may be indicative of sufficient perfusion. A perfusion index over 8% may be indicative of hyper-perfusion. The above equation is merely exemplary. Any other suitable method may be used to calculate an amount of perfusion in a tissue of a GI tract. The ranges above are also merely exemplary. The ranges may differ based on patient, location, measurement tool, equation used, or other factors.

Software application 12 may also use data from medical device 14 to characterize a thickness of tissue of a GI tract. For example, software application 12 may characterize a measure of an intestinal wall. Thickness may be characterized as a thickness score and may be expressed in terms of a percent value or in length units, such as millimeters. For healthy subjects, a jejunum or an ileum may have a thickness of approximately 1.1 mm-2 mm, a sigmoid colon may have a thickness of approximately 1.4 mm-3 mm, and an ascending colon may have a thickness of approximately 1.1 mm-2.5 mm. Increases in tissue thickness may be evaluated at regions of interest that show visible signs of inflammation such as, for example, redness, ulcerations, "cobblestoning," and/or strictures. Increases in tissue thickness may be measured in comparison to a previous baseline measurement made for that subject or from a measurement made at a healthy area located near the affected region. Differences in tissue thickness may be evaluated, and affected tissues can potentially show as 2-4 times thicker than healthy or baseline regions. A thickness score or a change in thickness score may be scaled to a sigmoid function.

In step 106, software application 12 may characterize inflammation of a healthy tissue sample, using the data collected and/or characterized in steps 102 and 104. For example, software application 12 may determine a measure of inflammation, which may be a reference inflammation score. Software application 12 may apply an operator or a function to a thickness score and perfusion index calculated in step 104, weight the results, and add the resulting values. For example, software application 12 may apply a sigmoid function to characterizations of perfusion and/or thickness, such as those described above. A sigmoid function applied in step 106 may be the special case of the logistic function defined by the following equation, where S(x) is the sigmoid function and e represents the mathematical constant "e":

$$S(x) = \frac{1}{1 + e^{-x}}$$

Software application 12 may calculate an inflammation score in step 106. An inflammation score ("I," in the equations below) may represent the amount of inflammation occurring in a tissue as a result of a disease, such as the diseases described above, and may account for both increased perfusion and increased tissue thickness. To calculate an inflammation score, a sigmoid function may be applied to a logarithm of a perfusion index and/or to a logarithm of a thickness. The sigmoid functions applied to the logarithm of a perfusion index and to a logarithm of a thickness may be weighted. For example, a sigmoid of a logarithm of a perfusion index may be weighted less than a sigmoid of a logarithm of a thickness. For example, a weighting factor of ⅓ may be applied to a sigmoid of a logarithm of a perfusion index, and a weighting factor of ⅔ may be applied to a sigmoid of a logarithm of a thickness. For example, an inflammation score may be calculated according to the below equation:

$$I = \{C_1 S(\log(P)) + C_2 S(\log(T))\} \times 100\%$$

where I is inflammation score (expressed in terms of a percentage), $C_1$ is a first constant, $C_2$ is a second constant, S(x) is the sigmoid function, P is a perfusion index, and T is a thickness score. A perfusion index (P) may be divided by 100 before plugging the perfusion index into the inflammation score equation above. $C_1$ in any of the equations herein may be equal to ⅓ or to 0.33. $C_2$ in any of the equations herein may be equal to ⅔ or to 0.67. These values of constants $C_1$ and $C_2$ are merely exemplary. The constants may have any suitable value which may be determined in any suitable manner. For example, the constants may be determined empirically based on a particular patient, a subset of patients, or the population as a whole. Expanding the above equation, the inflammation score may be calculated according to the below equation:

$$I = \left(C_1 \frac{1}{1+e^{-\log(P)}} + C_2 \frac{1}{1+e^{-\log(T)}}\right) \times 100\%$$

Any of the systems or methods described above may also be used to aggregate patient data. The systems or methods described above may compare information gathered from a particular patient to data collected from other patients and/or data manually input regarding patient classifications. For example, any of the systems or methods described above may make use of a library of conditions. The systems and methods described above may be used to stratify a patient with regard to their risk of exacerbation of a disease state. Such stratification may be based on previous data collected from a particular patient or may be based on data for a particular patient population or a patient population as a whole.

In step 108, a system such as system 10, described above with regard to FIG. 1, may obtain sample data from a tissue of a GI tract. For example, a medical device 14 of system 10 may be used to obtain such data. Data obtained in step 108 may have any of the characteristics of data obtained in step 102. For example, data obtained in step 108 may be indicative of an amount of light absorbed and/or reflected by a tissue. Data obtained in step 108 may pertain to tissue where fibrosis is suspected or where it is desired to evaluate a tissue for fibrosis. Data obtained in step 108 may be from the same subject as the data obtained in step 102, or it may be from a different subject.

In step 110, a component of system 10, such as software application 12, may characterize perfusion and/or tissue thickness of a sample tissue based on the data obtained in step 108. Step 110 may use any of the techniques described with regard to step 104 or may use alternative steps.

In step 112, software application 12 may characterize inflammation of a sample tissue, using the data collected and/or characterized in steps 108 and/or 110. For example, software application 12 may determine an inflammation score for the sample tissue. Step 112 may use any of the techniques discussed above with regard to step 106 or may use additional or alternative techniques.

In step 114, software application 12 may compare a sample inflammation score, such as that calculated in step 112 to a reference inflammation score, such as that calculated in 106. For example, software application 12 may determine the difference between the sample inflammation score and the reference inflammation score. In an alternative, software application 12 may determine a ratio of a sample inflammation score to a reference inflammation score. Any other metrics may be used to compare a reference inflammation score to a sample inflammation score. In an alternative, step 114 may be omitted.

In step 116, software application 12 may determine a fibrotic attribute of a sample tissue. In step 116, software application 12 may consider the results of earlier steps of method 100. Step 116 may also use any of the techniques described below, with regard to step 212 (see FIG. 3).

In step 116, software application 12 may consider a reference perfusion index and/or a reference thickness score (such as those determined in step 104), a reference inflammation score (such as that determined in step 106), a sample perfusion index and/or a sample thickness score (such as those determined in step 110), a sample inflammation score (such as that determined in step 112), and/or a comparison of reference and sample inflammation scores (such as that performed in step 114). For example, a perfusion index of 0.5%-5% and/or a thickness score of 1.2 mm-3 mm may fall into a "healthy" category and may be indicative of healthy tissue (more specific ranges for different portions of the GI tract are discussed above). A perfusion index of 5-10% and/or a thickness score of 3-10 mm may fall into a "fibrotic" category and be indicative of fibrotic tissue. A perfusion index of less than or equal to 5% or greater than or equal to 20% and/or a thickness score of 3-14 mm may fall into an "inflammation" category and be indicative of inflammation. An inflammation score of less than or equal to 50% may be indicative of healthy tissue. An inflammation score of greater than or equal to 50% may be indicative of fibrotic tissue or of inflammation and may indicate unhealthy tissue. Changes in perfusion index and thickness may be categorized into a plurality of classifications. For example, a change in perfusion index or thickness may be mild, moderate, or severe. A mild change may correspond to a "healthy" category described above. A moderate change may correspond to a "fibrotic" category described above. A severe change may correspond to an "inflammation" category described above.

As an example, software application 12 may determine whether an inflammation score is indicative of healthy tissue (e.g., inflammation score less than or equal to 50%) or unhealthy tissue (e.g., inflammation score above 50%). An inflammation score may serve as a composite score, and further review of underlying thickness scores and perfusion indices may only be necessary if an inflammation score is above 50%.

If an inflammation score is indicative of unhealthy tissue, then software application 12 may further analyze thickness score and/or perfusion index. If a perfusion index and a thickness score have increased at roughly the same rate, then a tissue may be characterized as having inflammation only, leading to edema. If a tissue thickness has increased at a higher rate than a perfusion index has increased, then the tissue may be categorized as fibrotic because more scarring has occurred, causing the tissue to thicken. In analyzing tissues, software application 12 may apply the categories described above: "healthy," "fibrotic," and "inflammation." In an alternative, software application 12 may apply categories such as "mild," "moderate," and "severe," as described above, where the categories increase in the direction from "mild" to "severe." A change in thickness in a higher category than a change in perfusion may be indicative of fibrotic tissue. On the other hand, a change in thickness in a similar category to a change in perfusion may be indicative of edema and/or inflammation. The values above are merely exemplary and are not limiting. Other values may be used, depending on the particular techniques used for determining a perfusion index, a thickness score, and/or an inflammation score. Values used may also depend on the characteristics of the subject or patient, the instruments used, or other factors.

Figure 4A:
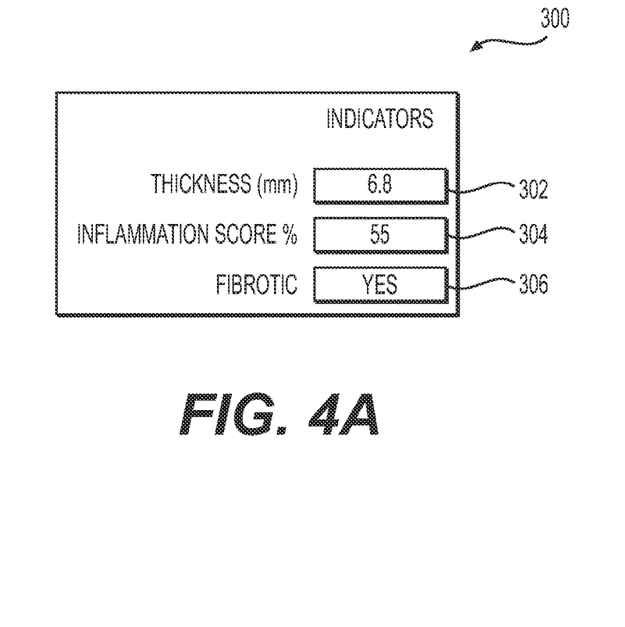
FIGS. 4A-4B depict exemplary user interfaces for displaying information about a disease state.
Figure 4B:
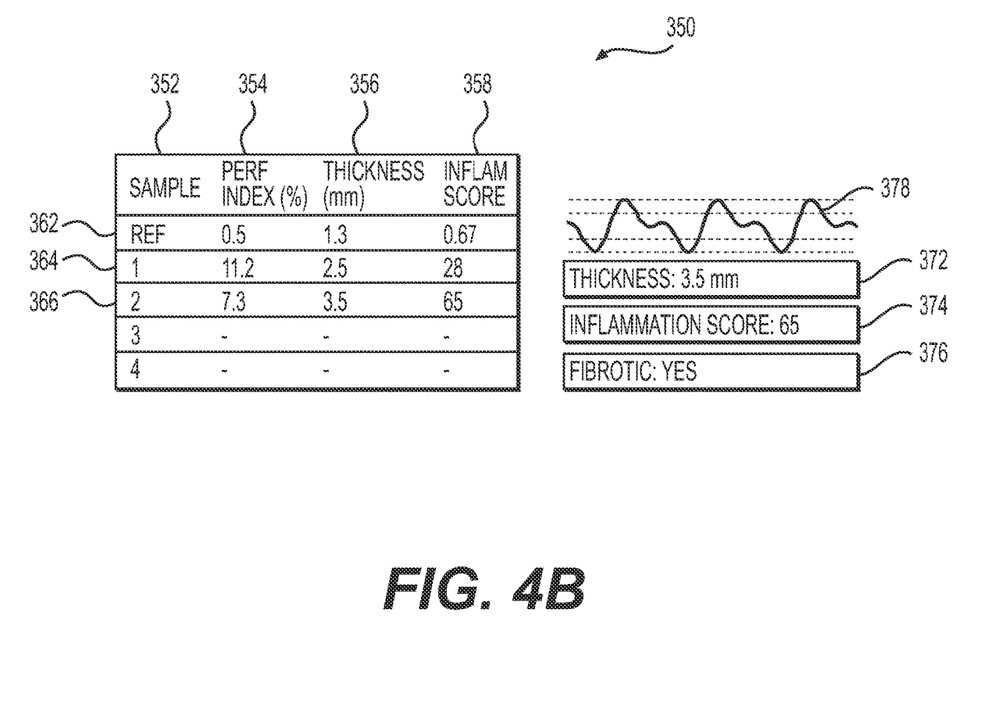

In step 118, results may be displayed on a graphical user interface such as user interface 16. Results displayed in step 118 may include results of any of the above steps or any other results. Results displayed in step 118 may be in the form of tables, graphs, charts, text, animations, or any other form. FIGS. 4A-4B, described in further detail below, show exemplary graphical user interface displays.

Figure 3:
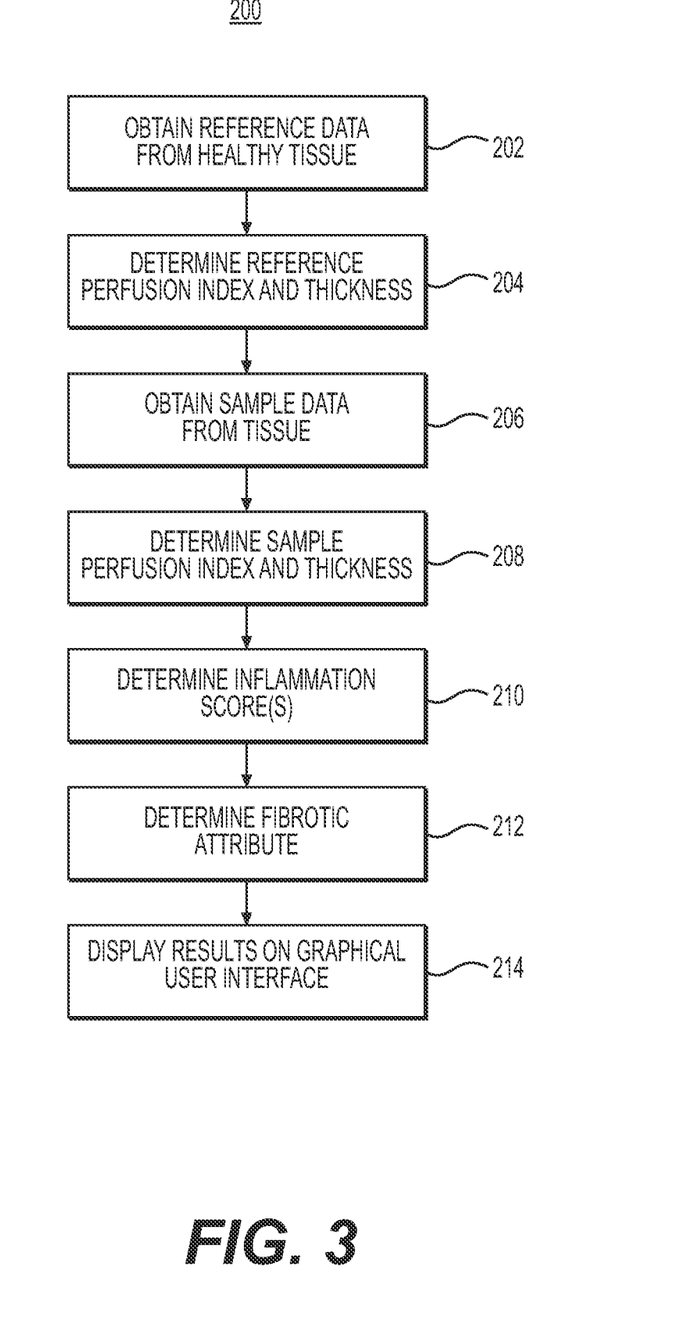

FIG. 3 shows an exemplary additional or alternative method 200 for evaluating characteristics of a GI tract. Method 200 may integrate any of the steps described above with regard to method 100. Steps of method 200 and method 100 may be combined or rearranged in any suitable combination. Certain steps of methods 200 and 100 may also be omitted.

In step 202, a system such as system 10, described above with regard to FIG. 1, may obtain reference data from healthy tissue of a GI tract. Any of the techniques described above with regard to step 102 may be performed to obtain reference data in step 202. In step 204, a component of system 10, such as software application 12, may characterize perfusion and/or tissue thickness of a healthy tissue based on the data obtained in step 202. Step 204 may make use of any of the techniques described in connection with step 104, described above. In step 206, a system such as system 10, described above with regard to FIG. 1, may obtain sample data from a tissue of a GI tract. Step 206 may implement any of the techniques described above with regard to steps 102, 108, and/or 202. In step 208, a component of system 10, such as software application 12, may characterize perfusion and/or tissue thickness of a sample tissue based on the data obtained in step 206. Step 208 may use any of the techniques described with regard to steps 104, 110, and/or 204, or may use alternative steps.

In step 210, software application 12 may determine one or more inflammation scores. Any of the techniques used in steps 106 and/or 112 may be used. In the alternative, instead of the function applied being a sigmoid function, a function applied may determine a change in perfusion index and/or thickness score. An inflammation score calculated in step 210 may involve calculating a difference in perfusion index between a reference perfusion index and/or reference thickness score characterized in step 204 and a sample perfusion index and/or sample thickness score characterized in step 208. The difference in thickness scores and/or difference in perfusion indexes may be weighted according to weighting factors. The weighting factors used in step 210 may be the same as or different from the weighting factors used in steps 106 and/or 112, discussed above. After weighting, the difference in thickness scores and/or difference in perfusion indexes may be added together to produce an inflammation score. For example, an inflammation score may be calculated according to the following equation:

$$I = C_1 \Delta P + C_2 \Delta T$$

where I is inflammation score (expressed in terms of a percentage), $C_1$ is a first constant, $C_2$ is a second constant, P is a perfusion index, and T is a thickness score. $C_1$ in any of the equations herein may be equal to $\frac{1}{3}$ or to 0.33. $C_2$ in any of the equations herein may be equal to $\frac{2}{3}$ or to 0.67. These values of constants $C_1$ and $C_2$ are merely exemplary. The constants may have any suitable value which may be determined in any suitable manner. For example, the constants may be determined empirically based on a particular patient, a subset of patients, or the population as a whole. An inflammation score of less than or equal to 25% may be indicative of remission. An inflammation score of 25% to 90% may be indicative of minor to moderate disease. An inflammation score of greater than 90% may be indicative of moderate to severe disease. The ranges above are merely exemplary. The ranges may differ based on patient, location, measurement tool, equation used, or other factors.

A change in perfusion index, $\Delta P$, may be calculated by subtracting a first perfusion index (e.g., the reference perfusion index determined in step 204) from a second perfusion index (e.g., the sample perfusion index determined in step 208). The result may be divided by the first perfusion index and multiplied by 100 in order to provide a change in perfusion index in terms of a percentage. For example, a change in perfusion index may be calculated using the following formula:

$$\Delta P = 100\left(\frac{P_n - P_{n-1}}{P_{n-1}}\right)$$

where $\Delta P$ is a change in perfusion index, $P_{n-1}$ is a first perfusion index, and $P_n$ is a second perfusion index. A change in perfusion index of less than or equal to 25% (as compared to a healthy reference sample) may be indicative of remission. A change in perfusion index of 25% to 90% may be indicative of minor to moderate disease. A change in perfusion index of greater than 90% may be indicative of moderate to severe disease. The ranges above are merely exemplary. The ranges may differ based on patient, location, measurement tool, equation used, or other factors.

A change in thickness score, $\Delta T$, may be calculated by subtracting a first thickness score (e.g., a reference thickness score determined in step 204) from a second thickness score (e.g., the sample thickness score determined in step 208). The result may be divided by the first thickness score and multiplied by 100 in order to provide a change in thickness score in terms of a percentage. For example, a change in thickness score may be calculated using the following formula:

$$\Delta T = 100\left(\frac{T_n - T_{n-1}}{T_{n-1}}\right)$$

where $\Delta T$ is a change in thickness score, $T_{n-1}$ is a first thickness score, and $T_n$ is a second thickness score. A thickness score or a change in thickness score may be scaled to a sigmoid function. Application of a sigmoid function may limit a score to within 0 to 1 (times 100%). Application of a sigmoid function may similarly limit an inflammation score incorporating a thickness score or a change in thickness score. A change in thickness score of less than or equal to 25% (as compared to a healthy reference sample) may be indicative of remission. A change in thickness score of 25% to 90% may be indicative of minor to moderate disease. A change in thickness score of greater than 90% may be indicative of moderate to severe disease.

In step 212, a fibrotic attribute of a tissue sample may be determined or otherwise characterized. A fibrotic attribute may be a measure of fibrosis in a tissue and may include a numerical or qualitative value assigned to fibrosis and may indicate a severity of fibrosis. In an alternative, a fibrotic attribute may be a "yes" or "no" indicator regarding the presence of fibrosis. A fibrotic attribute may also be an indicator of a tendency toward or away from fibrosis or of a degree of fibrosis. Step 212 may use any of the techniques of step 116, described above. In addition or in the alternative, a fibrotic attribute may be characterized using the values determined above, including inflammation score, change in thickness score, and change in perfusion index. As described above, an inflammation score may serve as a composite score. Further analysis of a change in thickness score and/or a change in perfusion if the inflammation score falls within certain ranges (e.g., above 50%, or above 25%). If an inflammation score is in a healthy range, then no further analysis may be needed.

In general, where a change in perfusion index is in a higher severity category than a change in thickness score, then a tissue may be flagged as fibrotic. As explained above, tissue thickening along with increased perfusion may be indicative of edema and/or inflammation. On the other hand, tissue thickening without increased perfusion may be indicative of scarring and fibrosis.

For example, if the inflammation score calculated in step 210 is greater than or equal to 25% (and thus indicative of at least minor disease), but the increase in perfusion is minimal, then the sample tissue may be characterized as fibrotic. Such an inflammation score would indicate a moderate thickness increase with little or no perfusion index increase. Although the overall inflammation score may be 25%, an increase in at least one of (a) thickness score and (b) perfusion index has occurred (because the inflammation score is a combination of the change in thickness score and the change in perfusion index). If thickness score has increased but perfusion has increased a minimal amount, scarring may have occurred. If an inflammation score calculated in step 210 is moderate to severe (that is, above 50%) and a perfusion index falls in a minor or a remission category, then tissue may also be characterized as fibrotic. If a change in perfusion index isn't large, but if a large increase in tissue thickness has occurred, scarring is likely because an increase in blood flow has occurred. Visually, a clinician may see a discoloration of tissue (e.g., tissue is less red) due to a lack of blood flow. If a thickness score and perfusion index are within the same severity category, then the sample tissue may be characterized as having inflammation but as not being fibrotic because the increases for perfusion index and thickness track similarly, indicating an increase in blood flow causing inflammation.

In step 214, results may be displayed on a graphical user interface such as user interface 16. Results displayed in step 214 may include results of any of the above steps or any other results. Results displayed in step 214 may be in the form of tables, graphs, charts, text, animations, or any other form. FIGS. 4A-4B, described in further detail below, show exemplary graphical user interface displays.

FIGS. 4A-4B show exemplary graphical user interfaces (GUIs) in accordance with this disclosure. FIG. 4A depicts an exemplary GUI 300. GUI 300 may be an output from step 118, as described with regard to FIG. 2. In the alternative, GUI 300 may be an output from step 214, as described with regard to FIG. 3, or an output from any other method. GUI 300 may depict information such as a thickness (and/or thickness score) 302, an inflammation score 304, and a fibrotic attribute 306. Thickness (and/or thickness score) 302 may be expressed in terms of length units, such as millimeters and may reflect a value determined in steps 110 and/or 208. Inflammation score 304 may be expressed in terms of a percentage and may reflect a value determined in steps 112 and/or 210. Fibrotic attribute 306 may be characterized by whether or not fibrosis is present and may reflect the outcome of steps 116 and/or 212. For example, fibrotic attribute 306 may be "yes," "no," or may indicate uncertainty or a tendency toward fibrosis or a lack of fibrosis.

FIG. 4B depicts an exemplary GUI 350. GUI 350 may be an output from step 214, as described above with regard to FIG. 3. In the alternative, GUI 350 may be an output from step 118, as described above with regard to FIG. 2. GUI 350 may display information regarding a sample identifier 352, a perfusion index 354, a thickness (and/or thickness score) 356, and/or an inflammation score 358. Perfusion index 354 may be indicative of values determined in steps 104, 110, 204, and/or 208. Thickness 356 may be indicative of values determined in steps 104, 110, 204 and/or 208. Inflammation score 358 may be indicative of values determined in steps 106, 112, and/or 210. Perfusion index 354 may be expressed in terms of a percentage. Thickness 356 may be expressed in terms of length units, such as millimeters. Inflammation score 358 may be expressed in terms of a percentage or may be unitless.

GUI 350 may display information for a reference tissue 362, and sample tissues 364, 366. GUI 350 may also depict information for a chosen sample, which may be, for example, a currently examined sample. For example, GUI 350 may depict a thickness 372, an inflammation score 374, and/or a fibrotic attribute 376 of a sample. As shown in FIG. 4B, thickness 372 and inflammation score 374 may correspond to a sample 366. GUI 350 may also depict other attributes of a sampled region. For example, GUI 350 may show a graph 378, which may depict activity of a region such as a slow wave activity. Such a waveform may be a plethysmograph, which may be used to depict perfusion measurements from optical sensors. A plethysmograph may be a slow waveform for a blood flow waveform. GUIs 300, 350 may also depict other information, further details of the information described above, or less information than described above.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A method for evaluating a gastrointestinal tract of a subject, the method comprising:
   positioning a sensor in a lumen of the gastrointestinal tract using a medical delivery device;
   using the sensor positioned in the subject to obtain data regarding qualities of a tissue of the gastrointestinal tract;
   using the obtained data, determining, by one or more processors in communication with the medical delivery device, a measure of perfusion of blood in the tissue;
   using the obtained data, determining, by the one or more processors, a measure of thickness of the tissue;
   using the measure of perfusion and the measure of thickness, determining, by the one or more processors, a measure of inflammation of the tissue; and
   using one or more of the measure of perfusion, the measure of thickness, and the measure of inflammation, classifying, by the one or more processors, a state of the tissue.

2. The method of claim 1, wherein classifying a state of the tissue includes classifying a fibrotic attribute of the tissue.

3. The method of claim 1, wherein the measure of perfusion is a perfusion index.

4. The method of claim 1, wherein determining a measure of inflammation comprises:
   applying a first function to the measure of perfusion; and
   applying a second function to the measure of thickness.

5. The method of claim 4, wherein determining a measure of inflammation further comprises adding a result of the first function and a result of the second function.

6. The method of claim 4, wherein applying the first function includes applying a weighting value.

7. The method of claim 4, wherein applying the first function includes applying a sigmoid function.

8. The method of claim 4, wherein applying the first function includes calculating a difference between the measure of perfusion and a reference measure of perfusion.

9. The method of claim 1, wherein using one or more of the measure of perfusion, the measure of thickness, and the measure of inflammation includes using each of the measure of perfusion, the measure of thickness, and the measure of inflammation.

10. The method of claim 1, wherein using the measure of perfusion, the measure of thickness, and the measure of inflammation comprises categorizing the measure of perfusion and categorizing the measure of inflammation.

11. The method of claim 1, further comprising comparing, by the one or more processors, the measure of inflammation to a reference measure of inflammation.

12. A method for evaluating a gastrointestinal tract, the method comprising:
    positioning a sensor in a lumen of the gastrointestinal tract using a medical delivery device;
    using the sensor positioned in a lumen of the gastrointestinal tract to obtain data regarding qualities of a tissue of the gastrointestinal tract;
    using the obtained data, determining, by a processor in communication with the medical delivery device, a measure of perfusion of blood in the tissue;
    using the obtained data, determining, by the processor in communication with the medical delivery device, a measure of thickness of the tissue; and
    using one or more of the measure of perfusion of blood in the tissue and the measure of thickness of the tissue, determining, by the processor in communication with the medical delivery device, a state of the tissue.

13. The method of claim 12, wherein determining the state of the tissue comprises:
    applying a function to one of the measure of perfusion of blood in the tissue or the measure of thickness of the tissue.

14. The method of claim 13, wherein applying the function includes applying a weighting value.

15. The method of claim 13, wherein the measure of perfusion is a perfusion index.

16. A method for evaluating a gastrointestinal tract, the method comprising:
    positioning a sensor in a lumen of the gastrointestinal tract using a medical delivery device;
    using the sensor positioned in a lumen of the gastrointestinal tract to obtain data regarding qualities of a tissue of the gastrointestinal tract;
    using the obtained data from the tissue, determining, by a processor in communication with the medical delivery device, a measure of perfusion of blood in the tissue;
    using the obtained data from the tissue, determining, by the processor in communication with the medical delivery device, a measure of thickness of the tissue;
    determining a sample inflammation score from the measure of perfusion and the measure of thickness of the tissue; and
    comparing the sample inflammation score to a reference inflammation score obtained from a healthy tissue.

17. The method of claim 16, wherein the tissue of the gastrointestinal tract and the healthy tissue are from a same patient.

18. The method of claim 16, wherein the tissue of the gastrointestinal tract and the healthy tissue are from different patients.

19. The method of claim 16, wherein the reference inflammation score is compiled from healthy tissue of multiple patients.

20. The method of claim 16, wherein the reference inflammation score obtained from the healthy tissue is from a library of patient data.

* * * * *